United States Patent
Rawlings et al.

(10) Patent No.: US 7,105,532 B2
(45) Date of Patent: Sep. 12, 2006

(54) PYRAZOLO[3,4-C]PYRIDINES AS GSK-3 INHIBITORS

(75) Inventors: Derek Anthony Rawlings, Welwyn (GB); Jason Witherington, Harlow (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 435 days.

(21) Appl. No.: 10/451,005

(22) PCT Filed: Dec. 19, 2001

(86) PCT No.: PCT/GB01/05663

§ 371 (c)(1),
(2), (4) Date: Nov. 20, 2003

(87) PCT Pub. No.: WO02/50073

PCT Pub. Date: Jun. 27, 2002

(65) Prior Publication Data

US 2004/0077681 A1    Apr. 22, 2004

(30) Foreign Application Priority Data

Dec. 19, 2000 (GB) ................ 00131070.6
May 25, 2001 (GB) ................ 0112800.8

(51) Int. Cl.
*A61K 31/4353* (2006.01)
*C07D 221/00* (2006.01)
(52) U.S. Cl. ............... 514/299; 546/112; 546/113; 514/300

(58) Field of Classification Search ............... 546/112, 546/113; 514/299, 300
See application file for complete search history.

(56) References Cited

U.S. PATENT DOCUMENTS

| | | | |
|---|---|---|---|
| 3,403,158 A | 9/1968 | Markille | |
| 6,610,677 B1 * | 8/2003 | Davies et al. | 514/183 |
| 6,638,926 B1 * | 10/2003 | Davies et al. | 514/217.05 |

FOREIGN PATENT DOCUMENTS

| | | |
|---|---|---|
| WO | 99/21859 | 5/1999 |
| WO | 01/81345 | 11/2001 |

* cited by examiner

*Primary Examiner*—Golam M. Shameem
(74) *Attorney, Agent, or Firm*—Kathryn L. Coulter; Amy H. Fix

(57) ABSTRACT

The present invention relates to novel compounds, in particular to novel pyrazolopyridine derivatives, to processes for the preparation of such compounds, to pharmaceutical compositions containing such compounds, and to the use of such compounds in medicine.

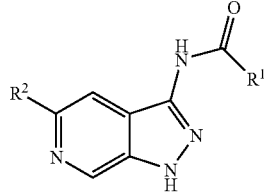

(I)

12 Claims, No Drawings

PYRAZOLO[3,4-C]PYRIDINES AS GSK-3 INHIBITORS

This application is filed pursuant to 35 U.S.C. § 371 as a United States National Phase Application of International Application No. PCT/GB01/05663 filed Dec. 19, 2001, which claims priority from 0031070.6 filed Dec. 19, 2000 and 00112800.8 filed May 25, 2001.

This invention relates to novel compounds, in particular to novel pyrazolopyridine derivatives, to processes for the preparation of such compounds, to pharmaceutical compositions containing such compounds and to the use of such compounds in medicine.

GSK-3 is a serine/threonine protein kinase composed of two isoforms (α and β) which are encoded by distinct genes. GSK-3 is one of several protein kinases which phosphorylates glycogen synthase (GS) (Embi et al. Eur. J. Biochem. (107) 519–527 (1980)). The α and β isoforms have a monomeric structure and are both found in mammalian cells. Both isoforms phosphorylate muscle glycogen synthase (Cross et al. Biochemical Journal (303) 21–26 (1994)) and these two isoforms show good homology between species (e.g. human and rabbit GSK-3α are 96% identical).

Type II diabetes (or Non-Insulin Dependent Diabetes Mellitus, NIDDM) is a multifactorial disease. Hyperglycaemia is due to insulin resistance in the liver, muscle and other tissues coupled with inadequate or defective secretion of insulin from pancreatic islets. Skeletal muscle is the major site for insulin-stimulated glucose uptake and in this tissue, glucose removed from the circulation is either metabolised through glycolysis and the TCA cycle, or stored as glycogen. Muscle glycogen deposition plays the more important role in glucose homeostasis and Type II diabetic subjects have defective muscle glycogen storage.

The stimulation of glycogen synthesis by insulin in skeletal muscle results from the dephosphorylation and activation of glycogen synthase (Villar-Palasi C. and Larner J. Biochim. Biophys. Acta (39) 171–173 (1960), Parker P J et al., Eur. J. Biochem. (130) 227–234 (1983), and Cohen P. Biochem. Soc. Trans. (21) 555–567 (1993)). The phosphorylation and dephosphorylation of GS are mediated by specific kinases and phosphatases. GSK-3 is responsible for phosphorylation and deactivation of GS, while glycogen bound protein phosphatase 1 (PP1G) dephosphorylates and activates GS. Insulin both inactivates GSK-3 and activates PP1G (Srivastava A K and Pandey S K Mol. and Cellular Biochem. (182) 135–141 (1998)).

Chen et al. Diabetes (43) 1234–1241 (1994) found that there was no difference in the mRNA abundance of PP1G between patients with Type II diabetes and control patients, suggesting that an increase in GSK-3 activity might be important in Type II diabetes. It has also recently been demonstrated that GSK-3 is overexpressed in Type II diabetic muscle and that an inverse correlation exists between skeletal muscle GSK-3α activity and insulin action (Nikoulina et al. Diabetes 2000, 49 263–271). Overexpression of GSK-3β and constitutively active GSK-3β (S9A, S9E) mutants in HEK-293 cells resulted in suppression of glycogen synthase activity (Eldar-Finkelman et al., PNAS (93) 10228–10233 (1996)) and overexpression of GSK-3β in CHO cells, expressing both insulin receptor and insulin receptor substrate 1 (IRS-1), resulted in an impairment of insulin action (Eldar-Finkelman and Krebs PNAS (94) 9660–9664 (1997)). Recent evidence for the involvement of elevated GSK-3 activity and the development of insulin resistance and type II diabetes in adipose tissue has emerged from studies undertaken in diabetes and obesity prone C57BL/6J mice (Eldar-Finkelman et al., Diabetes (48) 1662–1666 (1999)).

GSK-3 has been shown to phosphorylate other proteins in vitro including the eukaryotic initiation factor eIF-2B at Serine$^{540}$ (Welsh et al., FEBS Letts (421) 125–130 (1998)). This phosphorylation results in an inhibition of eIF-2B activity and leads to a reduction in this key regulatory step of translation. In disease states, such as diabetes, where there is elevated GSK-3 activity this could result in a reduction of translation and potentially contribute to the pathology of the disease.

Several aspects of GSK-3 functions and regulation in addition to modulation of glycogen synthase activity indicate that inhibitors of this enzyme may be effective in treatment of disorders of the central nervous system. GSK-3 activity is subject to inhibitory phosphorylation by PI 3 kinase-mediated or Wnt-1 class-mediated signals that can be mimicked by treatment with lithium, a low mM inhibitor of GSK-3 (Stambolic V., Ruel L. and Woodgett J. R. Curr. Biol. 1996 6(12): 1664–8).

GSK-3 inhibitors may be of value as neuroprotectants in treatment of acute stroke and other neurotraumatic injuries. Rôles for PI 3-kinase signalling through PKB/akt to promote neuronal cell survival are well established, and GSK-3 is one of a number of PKB/akt substrates to be identified that can contribute to the inhibition of apoptosis via this pathway (Pap & Cooper, (1998) J. Biol. Chem. 273: 19929–19932). Evidence suggests that astrocytic glycogen can provide an alternative energy source to facilitate neuronal survival under conditions of glucose deprivation (for example see Ransom, B. R. and Fern, R. (1997) Glia 21: 134–141 and references therein). Lithium is known to protect cerebellar granule neurons from death (D'Mello et al., (1994) Exp. Cell Res. 211: 332–338 and Volonte et al. (1994) Neurosci. Letts. 172: 6–10) and chronic lithium treatment has demonstrable efficacy in the middle cerebral artery occlusion model of stroke in rodents (Nonaka and Chuang, (1998) Neuroreport 9(9): 2081–2084). Wnt-induced axonal spreading and branching in neuronal culture models has been shown to correlate with GSK-3 inhibition (Lucas & Salinas, (1997) Dev. Biol. 192: 31–44) suggesting additional value of GSK-3 inhibitors in promoting neuronal regeneration following neurotraumatic insult.

Tau and β-catenin, two known in vivo substrates of GSK-3, are of direct relevance in consideration of further aspects of the value of GSK-3 inhibitors in relation to treatment of chronic neurodegenerative conditions. Tau hyperphosphorylation is an early event in neurodegenerative conditions such as Alzheimer's disease (AD), and is postulated to promote microtubule disassembly. Lithium has been reported to reduce the phosphorylation of tau, enhance the binding of tau to microtubules, and promote microtubule assembly through direct and reversible inhibition of glycogen synthase kinase-3 (Hong M., Chen D. C., Klein P. S. and Lee V. M. J.Biol. Chem. 1997 272(40) 25326–32). β-catenin is phosphorylated by GSK-3 as part of a tripartite complex with axin, resulting in β-catenin being targeted for degradation (Ikeda et al., (1998) EMBO J. 17: 1371–1384). Inhibition of GSK-3 activity is a key mechanism by which cytosolic levels of catenin are stabilised and hence promote β-catenin-LEF-1/TCF transcriptional activity (Eastman, Grosschedl (1999) Curr. Opin. Cell Biol. 11: 233). Rapid onset AD mutations in presenilin-1 (PS-1) have been shown to decrease the cytosolic β-catenin pool in transgenic mice. Further evidence suggests that such a reduction in available β-catenin may increase neuronal sensitivity to amyloid mediated death through inhibition of β-catenin-LEF-1/TCF transcriptional regulation of neuroprotective genes (Zhang et al., (1998) Nature 395: 698–702). A likely mechanism is suggested by the finding that mutant PS-1 protein confers decreased inactivation of GSK-3 compared with normal PS-1 (Weihl, C. C., Ghadge, G. D., Kennedy, S. G., Hay, N., Miller, R. J. and Roos, R. P.(1999) J. Neurosci. 19: 5360–5369).

International Patent Application Publication Number WO 97/41854 (University of Pennsylvania) discloses that an effective drug for the treatment of manic depression is lithium, but that there are serious drawbacks associated with this treatment. Whilst the precise mechanism of action of this drug for treatment of manic depression remains to be fully defined, current models suggest that inhibition of GSK-3 is a relevant target that contributes to the modulation of AP-1 DNA binding activity observed with this compound (see Manji et al., (1999) J. Clin. Psychiatry 60 (suppl 2): 27–39 for review).

GSK-3 inhibitors may also be of value in treatment of schizophrenia. Reduced levels of β-catenin have been reported in schizophrenic patients (Cotter D, Kerwin R, al-Sarraji S, Brion J P, Chadwich A, Lovestone S, Anderton B, and Everall I. 1998 Neuroreport 9:1379–1383) and defects in pre-pulse inhibition to startle response have been observed in schizophrenic patients (Swerdlow et al., (1994) Arch. Gen. Psychiat. 51: 139–154). Mice lacking the adaptor protein dishevelled-1, an essential mediator of Wnt-induced inhibition of GSK-3, exhibit both a behavioural disorder and defects in pre-pulse inhibition to startle response (Lijam N, Paylor R, McDonald M P, Crawley J N, Deng C X, Herrup K, Stevens K E, Maccaferri G, McBain C J, Sussman D J, and Wynshaw-Boris A. (1997) Cell 90: 895–905). Together, these findings implicate deregulation of GSK-3 activity as contributing to schizophrenia. Hence, small molecule inhibitors of GSK-3 catalytic activity may be effective in treatment of this mood disorder.

The finding that transient β-catenin stabilisation may play a role in hair development (Gat et al., Cell (95) 605–614 (1998)) suggests that GSK-3 inhibitors could be used in the treatment of baldness.

Studies on fibroblasts from the GSK-3β knockout mouse (Hoeflich KP et al., Nature 2000, 406, 86–90) support a role for this kinase in positively regulating the activity of NFkB. This transcription factor mediates cellular responses to a number of inflammatory stimuli. Therefore, pharmacologic inhibition of GSK-3 may be of use in treating inflammatory disorders through the negative regulation of NFkB activity.

The compounds of the present invention are pyrazolo[3,4-c]pyridines. Other pyrazolo[3,4-c]pyridines have previously been reported in the art. For example, U.S. Pat. No. 3,423,414 (B latter et al.) describes a series of pyrazolo[3,4-c]pyridines in which the C(7) position of the pyrazolopyridine ring is bisubstituted by H, alkyl or a combination thereof, or in which the C(7) position is substituted by an oxo group. The document provides no details regarding the mechanism of action of these compounds, nor does it contain biological data. It is suggested that such compounds have a potential therapeutic utility as anti-inflammatory agents.

We have now discovered that a series of pyrazolo[3,4-c]pyridines are particularly potent and selective inhibitors of GSK-3. These compounds are indicated to be useful for the treatment and/or prophylaxis of conditions associated with a need for inhibition of GSK-3, such as diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntingdon's disease, AIDS associated dementia, amyotrophic lateral sclerosis, multiple sclerosis and neurotraumatic diseases such as acute stroke, mood disorders such as schizophrenia and bipolar disorders, promotion of functional recovery post stroke, cerebral bleeding (for example, due to solitary cerebral amyloid angiopathy), hair loss, obesity, atherosclerotic cardiovascular disease, hypertension, polycystic ovary syndrome, syndrome X, ischaemia, traumatic brain injury, cancer, leukopenia, Down's syndrome, Lewy body disease, inflammation, and immunodeficiency.

Accordingly, in a first aspect, the present invention provides a compound of formula (I)

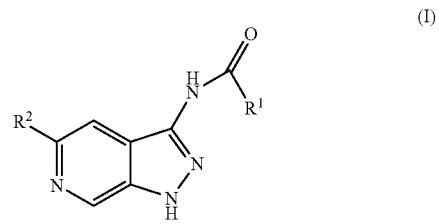

or a derivative thereof,
wherein;

$R^1$ is unsubstituted or substituted alkyl, unsubstituted or substituted cycloalkyl, unsubstituted or substituted alkenyl, unsubstituted or substituted cycloalkenyl, unsubstituted or substituted aryl, aralkyl wherein the aryl and the alkyl moieties may each independently be unsubstituted or substituted, aralkenyl wherein the aryl and alkenyl moieties may each independently be unsubstituted or substituted, unsubstituted or substituted heterocyclyl, or heterocyclylalkyl wherein the heterocyclyl and the alkyl moieties may each independently be unsubstituted or substituted; and $R^2$ is unsubstituted or substituted aryl or unsubstituted or substituted heteroaryl.

In a preferred aspect, there is provided a compound of formula (I) or a derivative thereof wherein $R^1$ is unsubstituted or substituted alkyl, unsubstituted or substituted cycloalkyl, unsubstituted or substituted aryl, unsubstituted or substituted heterocyclyl, or heterocyclylalkyl wherein the heterocyclyl and the alkyl moieties may each independently be unsubstituted or substituted; and wherein $R^2$ is unsubstituted or substituted aryl or unsubstituted or substituted heteroaryl.

When $R^1$ is unsubstituted or substituted alkyl, examples include $C_{1-6}$alkyl, for example methyl, ethyl, propyl, butyl and iso-propyl.

When $R^1$ is unsubstituted or substituted cycloalkyl, examples include $C_{3-8}$cycloalkyl, for example cyclopropyl and cyclopentyl.

When $R^1$ is unsubstituted or substituted alkenyl, examples include $C_{2-6}$alkenyl.

When $R^1$ is unsubstituted or substituted aryl, examples include phenyl.

When $R^1$ is unsubstituted or substituted aralkyl, examples include benzyl and phenethyl.

When $R^1$ is unsubstituted or substituted aralkenyl, examples include styryl.

When R¹ is unsubstituted or substituted heterocyclyl, examples include fluryl, pyridyl and piperidinyl. Suitably R¹ is piperidinyl.

When R¹ is unsubstituted or substituted heterocyclylalkyl, examples include piperidinylpropyl, piperazinylpropyl, morpholinylpropyl, pyrrolidinylpropyl and pyridylethyl. Suitably, R¹ is piperidinylpropyl, piperazinylpropyl and pyrrolidinylpropyl.

When R¹ is substituted alkyl, suitable substituents include halo, $C_{1-6}$alkoxy, carboxy, di($C_{1-6}$alkyl)amino and phenoxy.

When R¹ is substituted aryl, suitable substituents include up to five groups independently selected from the list consisting of hydroxy, $C_{1-6}$alkoxy, di($C_{1-6}$alkyl)amino, cyano, $C_{1-6}$alkyl, carboxy, $C_{1-6}$alkoxycarbonyl, $C_{1-6}$alkylaminocarbonyl, $C_{1-6}$alkylcarbonylamino, amino, halo, nitro and a subtituent —R³NR⁴R⁵ wherein R³ is $C_{1-6}$alkylene and R⁴ and R⁵ are $C_{1-6}$alkyl, or R³ is $C_{1-6}$alkylene and R⁴ and R⁵ together with the nitrogen atom to which they are attached form a hetrocyclic ring.

When R¹ is substituted heterocyclyl, suitable substituents include up to five groups independently selected from the list consisting of hydroxy, $C_{1-6}$alkoxy, di($C_{1-6}$alkyl)amino, cyano, $C_{1-6}$alkyl, carboxy, $C_{1-6}$alkoxycarbonyl, $C_{1-6}$alkylaminocarbonyl, $C_{1-6}$alkylcarbonylamino, amino, halo, nitro and a subtituent —R³NR⁴R⁵ wherein R³ is $C_{1-6}$ alkylene and R⁴ and R⁵ are $C_{1-6}$alkyl, or R³ is $C_{1-6}$alkylene and R⁴ and R⁵ together with the nitrogen atom to which they are attached form a hetrocyclic ring.

Suitably, R¹ is n-propyl, iso-propyl, cyclopropyl, cyclopentyl, 3-dimethylaminopropyl, 4-dimethylaminophenyl, 3-(pyrrolidin-1-yl)propyl, 3-(piperidin-1-yl)propyl, 3-(4-ethylpiperazin-1-yl)propyl, 1-methylpiperidin-4-yl and 4-[(pyrrolidin-1-yl)methyl]phenyl.

When R² is unsubstituted or substituted aryl, examples include phenyl.

When R² is unsubstituted or substituted heteroaryl, examples include pyridinyl, thienyl, furyl, quinolinyl and indolyl. Suitably, R² is pyridin-3-yl or quinolin-3-yl.

When R² is substituted aryl, suitable substituents include up to five groups independently selected from the list consisting of benzyloxy, halo, $C_{1-6}$alkyl, $C_{1-6}$alkoxy, $C_{1-3}$alkylenedioxy, $C_{1-6}$alkylcarbonylamino, perhalo$C_{1-6}$alkyl, nitro and perhalo$C_{1-6}$alkoxy.

When R² is substituted heteroaryl, suitable substituents include up to five groups independently selected from the list consisting of $C_{1-6}$alkoxy, halo, aryl and $C_{1-6}$alkyl. Suitably, R² is phenyl, 2-chlorophenyl, 2,3-difluorophenyl, 4-fluorophenyl, 2,3,4-trifluorophenyl, pyridin-3-yl, 5-phenylpyridin-3-yl, 6-methylpyridin-3-yl, 6-methyoxypyridin-3-yl and quinolin-3-yl.

In a further preferred aspect, there is provided a subset of compounds of formula (I) of formula (IA),

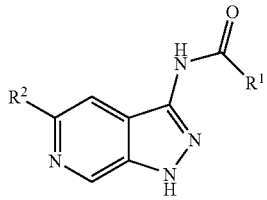

(IA)

or a derivative thereof,
wherein;

R¹ is $C_{1-6}$ alkyl, cyclo$C_{3-8}$ alkyl, di($C_{1-6}$ alkyl)aminoalkyl, phenyl optionally substituted by di($C_{1-6}$ alkyl)amino, heterocyclyl wherein the heterocyclyl moiety may be optionally substituted by $C_{1-6}$ alkyl and heterocyclyl$C_{1-6}$alkyl wherein the heterocyclyl moiety may be optionally substituted by $C_{1-6}$ alkyl and phenyl; and R² is phenyl optionally substituted by one or more halo atoms, quinolinyl and pyridinyl optionally susbtituted by $C_{1-6}$ alkyl, $C_{1-6}$ alkoxy and phenyl.

In a further preferred aspect of the present invention there is provided a subset of compounds of formula (I), wherein R¹ is n-propyl, iso-propyl, cyclopropyl, cyclopentyl, 3-dimethylaminopropyl, 4-dimethylaminophenyl, 3-(pyrrolidin-1-yl)propyl, 3-(piperidin-1-yl)propyl, 3-(4-ethylpiperazin-1-yl)propyl, 1-methylpiperidin-4-yl and 4-[(pyrrolidin-1yl)methyl]phenyl and wherein R² is as defined in formula (I).

In a further preferred aspect of the present invention there is provided a subset of compounds of formula (I), wherein R¹ is as defined in formula (I) and wherein R² is phenyl, 2-chlorophenyl, 2,3-difluorophenyl, 4-fluorophenyl, 2,3,4-trifluorophenyl, pyridin-3-yl, 5-phenylpyridin-3-yl, 6-methylpyridin-3-yl, 6-methoxypyridin-3-yl and quinolin-3-yl.

In still a further preferred aspect of the present invention there is provided a subset of compounds of formula (I), wherein R¹ is n-propyl, iso-propyl, cyclopropyl, cyclopentyl, 3-dimethylaminopropyl, 4-dimethylaminophenyl, 3-(pyrrolidin-1-yl)propyl, 3-(piperidin-1-yl)propyl, 3-(4-ethylpiperazin-1-yl)propyl, 1-methylpiperidin-4-yl and 4-[(pyrrolidin-1-yl)methyl]phenyl and wherein R² is phenyl, 2-chlorophenyl, 2,3-difluorophenyl, 4-fluorophenyl, 2,3,4-trifluorophenyl, pyridin-3-yl, 5-phenylpyridin-3-yl, 6-methylpyridin-3-yl, 6-methoxypyridin-3-yl and quinolin-3-yl.

Particularly preferred compounds of formula (I) which are of special interest as agents useful in the treatment and/or prophylaxis of conditions associated with a need for inhibition of GSK-3 are provided in Table 1 below.

Certain of the compounds of formula (I) may contain chiral atoms and/or multiple bonds, and hence may exist in one or more stereoisomeric forms. The present invention encompasses all of the stereoisomeric forms of the compounds of formula (I) whether as individual stereoisomers or as mixtures of stereoisomers, including geometric isomers and racemic modifications. Certain compounds of formula (I) may also exist as tautomers. The present invention encompasses all of the tautomeric forms of the compounds of formula (I).

Alkyl groups referred to herein, including those forming part of other groups, include straight or branched chain alkyl groups containing up to twelve, suitably up to six carbon atoms. These alkyl groups may be optionally substituted with up to five, suitably up to three, groups selected from the list consisting of aryl, heterocyclyl, alkylthio, alkenylthio, alkynylthio, arylthio, heterocyclylthio, alkoxy, arylalkoxy, arylalkylthio, amino, mono- or di-alkylamino, cycloalkyl, cycloalkenyl, carboxy and esters thereof, phosphonic acid and esters thereof, mono- or dialkylaminosulphonyl, aminosulphonyl, cyano, alkylcarbonylamino, arylcarbonylamino, arylaminocarbonyl, arylalkylaminocarbonyl, arylalkylcarbonylamino, thiazolidinedionyl, piperazinylcarbonyl wherein the piperazine may be unsubstituted or substituted, morpholinylcarbonyl, piperidinylcarbonyl, hydroxyalkylaminocarbonyl, dialkylaminocarbonyl, aminocarbonyl, dialkylaminoalkylaminocarbonyl, alkoxycarbonylamino, alkoxyalkylcarbonylamino, alkylcarbonylaminoalkylcarbonylamino, alkoxycarbonylalkylcarbonylamino, alkylaminocarbonyl, aminosulphonyl, arylsulphonylamino, alkylsulphonylamino, hydroxy, morpholinylalkylaminocarbonyl, hydroxyaminocarbonyl, aryloxy, heteroaryloxy, heteroarylalkoxy, heteroarylthio, heteroarylalkylthio and halogen.

Alkenyl and alkynyl groups referred to herein include straight and branched chain groups containing from two to twelve, suitably from two to six, carbon atoms. These alkenyl and alkynyl groups may be optionally substituted with up to five, suitably up to three, groups including those substituents described hereinbefore for the alkyl groups.

As used herein the term "carbocyclic" includes aromatic carbocyclic rings, for example aryl groups, and non-aromatic carbocyclic groups, for example cycloalkyl and cycloalkenyl groups, and fused carbocyclic ring systems wherein the carbocyclic rings may be aromatic or non-aromatic, for example indanyl.

Cycloalkyl and cycloalkenyl groups referred to herein include groups having between three and eight ring carbon atoms. These cycloalkyl and cycloalkenyl groups may be optionally substituted with up to five, suitably up to three, groups including those substituents hereinbefore described for the alkyl groups.

As used herein, the term "aryl" includes phenyl, naphthyl, and biphenyl groups, especially phenyl. Suitable optional substituents for any aryl group include up to five substituents selected from the list consisting of perhaloalkyl, arylaminocarbonyl, aralkyaminocarbonyl, hydroxyalkylaminocarbonyl, arylamino, aminosulphonyl, alkylsulphonylamino, mono- and di-alkylamino, mono- and di-alkylaminocarbonyl, arylaminocarbonylalkyl, arylcarbonyl, aralkoxy, heteroaryloxy, heteroarylalkoxy, heteroarylthio, heteroarylalkylthio, arylcarbonylamino, alkoxyalkylaminocarbonyl, aralkylcarbonylamino, aralkylcarbonylaminoalkyl, aminocarbonyl, morpholinylalkylaminocarbonylalkyl, arylaminosulphonyl, arylcarbonylaminoalkyl, arylsulphonylamino, aminocarbonylalkyl, hydroxyaminocarbonylalkyl, aryl, alkylcarbonylamino, alkylenedioxy, perhaloalkoxy, thiazolidinedionylalkyl, carboxyalkoxy, (methylpiperazinyl)carbonylalkyl, morpholinyl, morpholinylcarbonylalkyl, piperidinylcarbonylalkyl, hydroxyalkylaminocarbonylalkyl, mono- and di-alkylaminocarbonylalkyl, alkoxyalkylaminosulphonyl, alkoxyamino, perhaloalkylcarbonylamino, alkylaminosulphonylalkyl, mono- and di-alkylaminoalkylaminocarbonylalkyl, carboxyalkoxy, alkoxycarbonylaminoalkyl, aminocarbonylalkenyl, alkoxyalkylcarbonylamino, alkylcarbonylaminoalkylcarbonylamino, alkylcarbonylaminoalkyl, hydroxyalkylcarbonylamino, alkoxycarbonylalkylcarbonylamino, carboxyalkylcarbonylamino, alkoxyalkylcarbonylaminoalkyl, alkylcarbonylaminoalkylcarbonylamino, hydroxyalkylcarbonylaminoalkyl, carboxyalkenyl, aminocarbonylalkylcarbonylamino, alkylaminocarbonylalkoxy, alkylaminosulphonylalkyl, aminocarbonylalkyl, oxazolyl, pyridinylalkylcarbonylamino, methyloxazolyl, alkylthio, alkylaminocarbonylalkyl, halo, alkyl, alkenyl, substituted alkenyl, arylalkyl, alkoxy, alkoxyalkyl, haloalkyl, haloalkyloxy, hydroxy, hydroxyalkyl, nitro, amino, cyano, cyanoalkyl, mono- and di-N-alkylamino, acyl, acylamino, N-alkylacylamino, acyloxy, carboxy, carboxyalkyl, carboxyalkylcarbonyl, carboxyalkenyl, ketoalkylester, carbamoyl, carbamoylalkyl, mono- and di-N-alkylcarbamoyl, alkoxycarbonyl, alkoxycarbonylalkyl, aryloxy, arylthio, aralkyloxy, aryloxycarbonyl, ureido, guanidino, morpholino, adamantyl, oxazolyl, aminosulphonyl, alkylaminosulphonyl, alkylthio, haloalkylthio, alkylsulphinyl, alkylsulphonyl, cycloalkyl, heterocyclyl, heterocyclylalkyl, alkoxycarbonyl, trityl, substituted trityl, mono- or bis-alkylphosphonate or mono- or bis-alkylphosphonate$C_{1-6}$alkyl or any two adjacent substituents on the phenyl ring together with the carbon atoms to which they are attached form a carbocyclic ring or a heterocyclic ring.

As used herein the terms "heterocyclyl" and "heterocyclic" suitably include, unless otherwise defined, aromatic and non-aromatic, single and fused, rings suitably containing up to four heteroatoms in each ring, each of which is selected from oxygen, nitrogen and sulphur. Each ring suitably has from 4 to 7, preferably 5 or 6, ring atoms. These heterocyclyl and heterocyclic rings may be unsubstituted or substituted by up to five substituents. A fused heterocyclic ring system may include carbocyclic rings and need include only one heterocyclic ring. Examples include furyl, piperazinyl, thienyl, piperidinyl, pyridazinyl, morpholinyl, pyridyl, indolinyl, quinolinyl, indolyl, benzoxazolyl, benzothiazolyl, benzothiazolinonyl, and benzoxazolinonyl. Suitable substituents for any heterocyclyl or heterocyclic group are selected from cyano, carboxyalkoxy, morpholinyl, hydroxyalkylaminocarbonyl, alkoxyalkylaminosulphonyl, alkylaminosulphonyl, arylcarbonylamino, aralkylcarbonylamino, aralkenylcarbonylamino, perhalocarbonylamino, perhaloalkyl, aminocarbonyl, nitro, aminocarbonylalkenyl, alkoxyalkylcarbonylamino, alkylcarbonylaminoalkylcarbonylamino, hydroxyalkylcarbonylamino, carboxyalkenyl, aminocarbonylalkylcarbonylamino, alkylaminocarbonylalkoxy, aryl, arylcarbonyl, alkylenedioxy, aryloxy, aralkyloxy, perhaloalkylthio, alkcylcarbonyl, alkoxycarbonylalkylthio, carboxyalkylthio, hydroxyalkyl, alkoxyalkyl, cyanoalkyl, carboxyalkyl, alkoxycarbonyl, halogen, alkyl, arylalkyl, alkoxy, alkoxyalkyl, haloalkyl, hydroxy, amino, mono- and di-N-alkylamino, acylamino, carboxy and salts and esters thereof, carbamoyl, mono- and di-N-alkylaminocarbonyl, aryloxycarbonyl, alkoxycarbonylalkyl, aryl, oxy groups, ureido, guanidino, sulphonylamino, aminosulphonyl, alkylthio, alkylsulphinyl, alkylsulphonyl, cyano, hydroxy, alkylcarbonylamino, heterocyclyl and heterocyclylalkyl.

As used herein the term "heteroaryl" suitably includes, unless otherwise defined, aromatic single and fused rings suitably containing up to four heteroatoms in each ring, each of which is selected from oxygen, nitrogen and sulphur. Each ring suitably has from 4 to 7, preferably 5 or 6, ring atoms. These heteroaryl rings may be unsubstituted or substituted by up to five substituents. A fused heteroaryl ring system may include carbocyclic rings and need include only one heteroaryl ring. Examples include furyl, thienyl, pyridazinyl, pyridyl, quinolinyl, indolyl, benzoxazolyl, and benzothiazolyl. Suitable substituents for any heteroaryl group are selected from cyano, carboxyalkoxy, morpholinyl, hydroxyalkylaminocarbonyl, alkoxyalkylaminosulphonyl, alkylaminosulphonyl, arylcarbonylamino, aralkylcarbonylamino, aralkenylcarbonylamino, perhalocarbonylamino, perhaloalkyl, aminocarbonyl, nitro, aminocarbonylalkenyl, alkoxyalkylcarbonylamino, alkylcarbonylaminoalkylcarbonylamino, hydroxyalkylcarbonylamino, carboxyalkenyl, aminocarbonylalkylcarbonylamino, alkylaminocarbonylalkoxy, aryl, arylcarbonyl, alkylenedioxy, aryloxy, aralkyloxy, perhaloalkylthio, alkylcarbonyl, alkoxycarbonylalkylthio, carboxyalkylthio, hydroxyalkyl, alkoxyalkyl, cyanoalkyl, carboxyalkyl, alkoxycarbonyl, halogen, alkyl, arylalkyl, alkoxy, alkoxyalkyl, haloalkyl, hydroxy, amino, mono- and di-N-alkylamino, acylamino, carboxy and salts and esters thereof, carbamoyl, mono- and di-N-alkylaminocarbonyl, aryloxycarbonyl, alkoxycarbonylalkyl, aryl, oxy groups, ureido, guanidino, sulphonylamino, aminosulphonyl, alkylthio, alkylsulphinyl, alkylsulphonyl, cyano, hydroxy, alkylcarbonylamino, heterocyclyl and heterocyclylalkyl.

As used herein the terms "halogen" or "halo" include iodo, bromo, chloro or fluoro, especially chloro or fluoro.

Suitable derivatives of the compounds of the invention are pharmaceutically acceptable derivatives.

Suitable derivatives of the compounds of the invention include salts and solvates.

Suitable pharmaceutically acceptable derivatives include pharmaceutically acceptable salts and pharmaceutically acceptable solvates.

Suitable pharmaceutically acceptable salts include metal salts, such as for example aluminium, alkali metal salts such as lithium, sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)amine or tri-(2-hydroxyethyl)amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine, quinine or quinoline.

Suitable pharmaceutically acceptable salts also includes pharmaceutically acceptable acid addition salts, such as those provided by pharmaceutically acceptable inorganic acids or organic acids.

Suitable pharmaceutically acceptable acid addition salts provided by pharmaceutically acceptable inorganic acids includes the sulphate, nitrate, phosphate, borate, hydrochloride and hydrobromide and hydroiodide.

Suitable pharmaceutically acceptable acid addition salts provided by pharmaceutically acceptable organic acids includes the acetate, tartrate, maleate, fumarate, malonate, citrate, succinate, lactate, toluene sulphonate, trifluoroacetate, oxalate, benzoate, ascorbate, methanesulphonate, α-keto glutarate and α-glyerophosphate.

Suitable pharmaceutically acceptable solvates include hydrates.

For the avoidance of doubt when used herein the term "diabetes" includes diabetes mellitus, especially Type 2 diabetes, and conditions associated with diabetes mellitus.

The term "conditions associated with diabetes" includes those conditions associated with the pre-diabetic state, conditions associated with diabetes mellitus itself and complications associated with diabetes mellitus.

The term "conditions associated with the pre-diabetic state" includes conditions such as insulin resistance, impaired glucose tolerance and hyperinsulinaemia.

The term "conditions associated with diabetes mellitus itself" include hyperglycaemia, insulin resistance and obesity. Further conditions associated with diabetes mellitus itself include hypertension and cardiovascular disease, especially atherosclerosis and conditions associated with insulin resistance. Conditions associated with insulin resistance include polycystic ovarian syndrome and steroid induced insulin resistance.

The term "complications associated with diabetes mellitus" includes renal disease, especially renal disease associated with Type II diabetes, neuropathy and retinopathy. Renal diseases associated with Type II diabetes include nephropathy, glomerulonephritis, glomerular sclerosis, nephrotic syndrome, hypertensive nephrosclerosis and end stage renal disease.

A further aspect of the invention provides a process for the preparation of a compound of formula (I), or a derivative thereof, which process comprises reaction of a compound of formula (II),

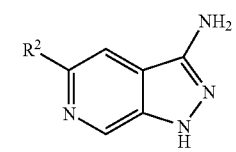

(II)

wherein;

$R^2$ is as defined in formula (I), with a compound of formula (III),

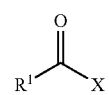

(III)

wherein;

$R^1$ is as defined in formula (I) and X is a leaving group, and thereafter, if required, carrying out one or more of the following optional steps:
(i) converting a compound of formula (I) to a further compound of formula (I);
(ii) removing any necessary protecting group;
(iii) preparing an appropriate derivative of the compound so formed.

Examples of suitable leaving groups, X, are chloro and acyloxy.

The reaction between the compounds of formulae (II) and (III) is carried out in a suitable solvent under conventional amidation conditions a suitable temperature providing a suitable rate of formation of the required product, generally an elevated temperature, over a suitable reaction time. Suitable solvents include pyridine. Suitable reaction temperatures include those in the range of 60° C. to 220° C. and, as appropriate, the reflux temperature of the solvent. Suitable reaction times are those in the range 12–96 hours. If the compound of formula (II) is a weak nucleophile, then the reaction may be assisted by, for example, using temperatures at the upper end of this range, or by using a hindered base catalyst such as dimethylaminopyridine (DMAP). A hindered base is a base which does not act as a competing nucleophile. The reaction products are isolated using conventional methods. Typically, the reaction mixture is cooled, the residue concentrated and the product purified by conventional methods such as crystallisation, chromatography, purification by ion-exchange filtration or trituration. Suitable methods of chromatography include, for example, silica gel chromatography, and reverse-phase preparative HPLC. Suitable ion-exchange resins include acid ion-exchange resins, for example, SCX resin. It will be appreciated that the purification of a compound of formula (I) may require more than one chromatography step and may additionally require purification with a suitable ion-exchange resin. Conventional methods of heating and cooling may be employed, for example, thermostatically controlled oil baths and ice/salt baths respectively. Crystalline product may be obtained by standard methods.

Compounds of formula (II) are believed to be novel and accordingly form a further aspect of the invention.

In the reaction of a compound of formula (II) with a compound of formula (III), a compound of formula (V) may be formed,

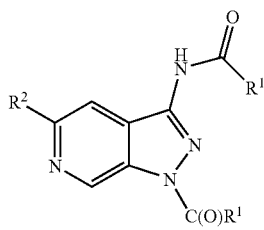

(V)

wherein;

R¹ and R² are as hereinbefore defined.

A compound of formula (V) may be converted into a compound of formula (I) either in situ or in a separate step, by reaction with a suitable nucleophile, such as piperidine or a polyamine resin.

Thus, according to the present invention there is provided a process for the preparation of a compound of formula (I) or a derivative thereof, which process comprises reaction of a compound of formula (V), as defined hereinbefore, with a nucleophile, and thereafter, if required, carrying out one or more of the following optional steps:

(i) converting a compound of formula (I) to a further compound of formula (I);
(ii) removing any necessary protecting group;
(iii) preparing an appropriate derivative of the compound so formed.

Compounds of formula (V) are considered to be novel and accordingly form a further aspect of the invention.

In a preferred aspect, the compound of formula (III) is added to a solution of the compound of formula (II) in pyridine. The reaction mixture is stirred at reflux for 17 hours, allowed to cool, and concentrated. The crude product is purified by chromatography, for example, silica gel chromatography.

The above mentioned conversion of a compound of formula (I) into another compound of formula (I) includes any conversion which may be effected using conventional procedures, but in particular the said conversions include any combination of:

(i) converting one group R¹ into another group R¹;
(ii) converting one group R² into another group R².

The above mentioned conversions (i) and (ii) may be carried out using any appropriate method under conditions determined by the particular groups chosen.

The above mentioned conversions may as appropriate be carried out on any of the intermediate compounds mentioned herein.

Suitable protecting groups in any of the above mentioned reactions are those used conventionally in the art. The methods of formation and removal of such protecting groups are those conventional methods appropriate to the molecule being protected. Thus for example a benzyloxy group may be prepared by treatment of the appropriate compound with a benzyl halide, such as benzyl bromide, and thereafter, if required, the benzyl group may be conveniently removed using catalytic hydrogenation or a mild ether cleavage reagent such as trimethylsilyl iodide or boron tribromide. Where appropriate individual isomeric forms of the compounds of formula (I) may be prepared as individual isomers using conventional procedures.

The absolute stereochemistry of compounds may be determined using conventional methods, such as X-ray crystallography.

The derivatives of the compounds of formula (I), including salts and/or solvates, may be prepared and isolated according to conventional procedures.

Compounds of formula (II) may be prepared by reaction of a compound of formula (IV)

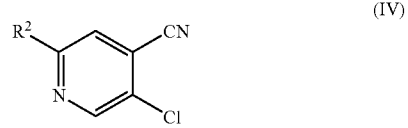

(IV)

wherein;

R² is as defined in formula (I), with hydrazine, or a hydrate thereof.

The reaction between the compound of formula (I) and hydrazine, or a hydrate thereof, is carried out in a suitable solvent at a suitable temperature providing a suitable rate of formation of the required product, generally an elevated temperature, over a suitable reaction time. Suitable solvents include pyridine. Suitable reaction temperatures include those in the range of 60° C. to 220° C. and, as appropriate, the reflux temperature of the solvent. Suitable reaction times are those in the range 1–8 hours. The reaction products are isolated using conventional methods. Typically, the reaction mixture is cooled, the product isolated by filtration, and dried. Conventional methods of heating and cooling may be employed, for example electric heating mantles and ice/salt baths respectively. The reaction products may, if desired, be purified by conventional methods, such as crystallisation, chromatography and trituration.

In a preferred aspect, hydrazine hydrate is added to a stirred solution of the compound of formula (I) in pyridine. The reaction mixture is stirred at reflux for 3 hours and cooled. The crude product is purified by chromatography.

Compounds of formula (IV) may be prepared from 2,5-dichloro-isonicotinonitrile (WO 96/33975) employing conventional cross-coupling procedures disclosed in standard reference texts of synthetic methodology such as March's Advanced Organic Chemistry: Reactions Mechanisms, and Structures, 5th Edition, Wiley, 2001.

Compounds of formula (III) are either commercially available, or are prepared by analogy with known conventional literature procedures, for example those disclosed in standard reference texts of synthetic methodology such as March's Advanced Organic Chemistry: Reactions, Mechanisms, and Structures, 5th Edition, Wiley, 2001.

As stated above, the compounds of formula (I), or pharmaceutically acceptable derivatives thereof, are indicated to be useful as inhibitors of GSK-3.

The invention therefore provides a compound of formula (I), or a pharmaceutically acceptable derivative thereof, for use as an inhibitor of GSK-3.

Accordingly, the present invention also provides a method for the treatment of conditions associated with a need for inhibition of GSK-3 such as diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntingdon's disease, AIDS associated dementia, amyotrophic lateral sclerosis, multiple sclerosis and neurotraumatic diseases such as acute stroke, mood disorders such as schizophrenia and bipolar disorders, promotion of functional recovery post stroke, cerebral bleeding (for example, due to solitary cerebral amyloid angiopathy), hair loss, obesity, atherosclerotic cardiovascular disease, hypertension, polycystic ovary syndrome, syndrome X, ischaemia, traumatic brain injury, cancer, leukopenia, Down's syndrome, Lewy body disease, inflammation, and immunodeficiency, which method comprises the administration of a pharmaceutically effective, non-toxic amount of a compound of formula (I) or a pharmaceutically acceptable derivative thereof, The present invention further provides a compound of formula (I), or a pharmaceutically acceptable derivative thereof, for use as an inhibitor of glycogen synthase kinase-3, and especially for use in the treatment of conditions associated with a need for the inhibition of GSK-3, such as diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntingdon's disease, AIDS associated dementia, amyotrophic lateral sclerosis, multiple sclerosis and neurotraumatic diseases such as acute stroke, mood disorders such as schizophrenia and bipolar disorders, promotion of functional recovery post stroke, cerebral bleeding (for example, due to solitary cerebral amyloid angiopathy), hair loss, obesity, atherosclerotic cardiovascular disease, hypertension, polycystic ovary syndrome, syndrome X, ischaemia, traumatic brain injury, cancer, leukopenia, Down's syndrome, Lewy body disease, inflammation, and immunodeficiency.

The present invention also provides the use of a compound of formula (I), or a pharmaceutically acceptable derivative thereof, for the manufacture of a medicament for the treatment of conditions associated with a need for the inhibition of GSK-3, such as diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntingdon's disease, AIDS associated dementia, amyotrophic lateral sclerosis, multiple sclerosis and neurotraumatic diseases such as acute stroke, mood disorders such as schizophrenia and bipolar disorders, promotion of functional recovery post stroke, cerebral bleeding (for example, due to solitary cerebral amyloid angiopathy), hair loss, obesity, atherosclerotic cardiovascular disease, hypertension, polycystic ovary syndrome, syndrome X, ischaemia, traumatic brain injury, cancer, leukopenia, Down's syndrome, Lewy body disease, inflammation, and immunodeficiency.

In a further aspect of this invention, there is provided a compound of formula (I), or a pharmaceutically acceptable derivative thereof, for use as an active therapeutic substance.

Preferably, the compounds of formula (I), or pharmaceutically acceptable derivatives thereof, are administered as pharmaceutically acceptable compositions.

Accordingly, the invention also provides a pharmaceutical composition which comprises a compound of formula (I), or a pharmaceutically acceptable derivative thereof, and a pharmaceutically acceptable carrier.

The active compounds are usually administered as the sole medicament agent but they may be administered in combination with other medicament agents as dictated by the severity and type of disease being treated. For example in the treatment of diabetes, especially Type 2 diabetes, a compound of formula (I), or a pharmaceutically acceptable derivative thereof, may be used in combination with other medicament agents, especially antidiabetic agents such as insulin secretagogues, especially sulphonylureas, insulin sensitisers, especially glitazone insulin sensitisers (for example thiazolidinediones), or with biguanides or alpha glucosidase inhibitors or the compound of formula (I), or a pharmaceutically acceptable derivative thereof, may be administered in combination with insulin.

The said combination comprises co-administration of a compound of formula (I), or a pharmaceutically acceptable derivative thereof, and an additional medicament agent or the sequential administration of a compound of formula (I), or a pharmaceutically acceptable derivative thereof, and the additional medicament agent.

Co-administration includes administration of a pharmaceutical composition which contains both a compound of formula (I), or a pharmaceutically acceptable derivative thereof, and the additional medicament agent or the essentially simultaneous administration of separate pharmaceutical compositions of a compound of formula (I), or a pharmaceutically acceptable derivative thereof, and the additional medicament agent.

The compositions of the invention are preferably adapted for oral administration. However, they may be adapted for other modes of administration. The compositions may be in the form of tablets, capsules, powders, granules, lozenges, suppositories, reconstitutable powders, or liquid preparations, such as oral or sterile parenteral solutions or suspensions. In order to obtain consistency of administration it is preferred that a composition of the invention is in the form of a unit dose. Preferably the compositions are in unit dosage form. A unit dose will generally contain from 0.1 to 1000 mg of the active compound.

Generally an effective administered amount of a compound of the invention will depend on the relative efficacy of the compound chosen, the severity of the disorder being treated and the weight of the sufferer. However, active compounds will typically be administered once or more times a day for example 2, 3 or 4 times daily, with typical total daily doses in the range of from 0.1 to 800 mg/kg/day.

Suitable dose forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The formulations mentioned herein are carried out using standard methods such as those described or referred to in reference texts such as the British and US Pharmacopoeias, Remington's Pharmaceutical Sciences (Mack Publishing Co.), Martindale The Extra Pharmacopoeia (London, The Pharmaceutical Press) or the above mentioned publications.

Suitable methods for preparing and suitable unit dosages for the additional medicament agent, such as the antidiabetic agent mentioned herein include those methods and dosages described or referred to in the above mentioned reference texts.

GSK-3 Assay

GSK-3 assays used to test the compounds of the invention include the following protocol which is based on the ability of the kinase to phosphorylate a biotinylated 27 mer peptide, Biot- KYRRAAVPPSPSLSRHSSPHQ(S)EDEEE, the sequence of which is derived from the phosphorylation site of glycogen synthase, where (S) is a pre-phosphorylated serine as in glycogen synthase in vivo and the three consensus sites for GSK-3 specific phosphorylation are underlined. The phosphorylated biotinylated peptide is then captured onto Streptavidin coated SPA beads (Amersham Technology), where the signal from the $^{33}$P is amplified via the scintillant contained in the beads.

Using microtitre plates, GSK-3 was assayed in 50 mM MOPS buffer, pH 7.0, containing 5% glycerol, 0.01% Tween-20, 7.5 mM 2-mercaptoethanol, 10 mM magnesium acetate, 8 uM of the above peptide, and 10 uM [$^{33}$P]-ATP. After incubation at room temperature, the reaction was stopped by addition of 50 mM EDTA solution containing the Streptavidin coated SPA beads to give a final 0.2 mgs. Following centrifugation, the microtitre plates are counted in a Trilux 1450 microbeta liquid scintillation counter (Wallac). IC$_{50}$ values are generated for each compound by fitting to a four parameter model.

The most potent compounds of the present invention show IC$_{50}$ values in the range of 1 to 500 nM.

No adverse toxicological effects are expected for the compounds of the invention, when administered in accordance with the invention.

The following Descriptions and Examples illustrate the invention, but do not limit it in any way.

SYNTHETIC METHOD A

EXAMPLE 1

N-(5-Phenyl-1H-pyrazolo[3,4c]pyridin-3-yl)butyramide n-Butyric anhydride (70 uL, 0.43 mmol) was added to a solution of 5-phenyl-1H-pyrazolo[3,4-c]pyridin-3-ylamine (90 mg, 0.43 mmol) in pyridine (0.5 mL). The reaction mixture was stirred at reflux for 17 hours, allowed to cool and concentrated. Purification by column chromatography using 4% v/v methanol in chloroform as eluent afforded the title compound as a solid.

MS (APCI+ve): [M+H]$^+$ at m/z 281 (C$_{16}$H$_{16}$N$_4$O) requires [M+H]$^+$ at m/z 281.

$^1$H NMR δ (DMSO-d$_6$) 13.4 (1H, br), 10.8 (1H, s), 9.1 (1H, s), 8.3 (1H, s), 8.0 (2H, d), 7.6–7.4 (3H, m), 2.4 (2H, t), 1.6 (2H, q), 1.0 (3H, t).

The starting material for Example 1 may be prepared according to Descriptions 1 & 2 below.

Description 1

5-Chloro-2-phenyl-isonicotinonitrile

Tetralds(triphenylphosphine)palladium(0) (167 mg, 0.14 mmol) was added to a stirred solution of phenylboronic acid (423 mg, 3.47 mmol), 2,5-dichloro-isonicotinonitrile (550 mg, 2.89 mmol) and sodium carbonate (3.5 mL of 2M aqueous solution) in dimethoxyethane (7 mL) and ethanol (3.5 mL). The resulting suspension was stirred at reflux for 3 hours, concentrated in vacuo and water (25 mL) added. The aqueous solution was extracted with ethyl acetate (×3) and the combined organic extracts were washed with brine, dried and concentrated. Purification by column chromatography using 2% v/v ethyl acetate in hexane as eluent afforded the title compound as a solid.

MS (APCI+ve): [M+H]$^+$ at m/z 215 (C$_{12}$H$_7$ClN$_2$) requires [M+H]$^+$ at m/z 215.

$^1$H NMR δ (CDCl$_3$) 8.8 (1H, s), 8.1–7.9 (3H, m), 7.6–7.4 (3H, m).

Description 2

5-Phenyl-1H-pyrazolo[3,4-c]pyridin-3-ylamine

Hydrazine hydrate (0.3 mL, 5.9 mmol) was added to a stirred solution of 5-chloro-2-phenyl-isonicotinonitrile (420 mg, 1.9 mmol) in pyridine (5 mL). The reaction mixture was stirred at reflux for 3 hours, cooled and the resulting solid was filtered and dried in vacuo, affording a crude residue. Purification by column chromatography using a gradient elution of 0–5% methanol in dichloromethane as eluent afforded the title compound as a solid.

$^1$H NMR δ (DMSO-d$_6$) 11.9 (1H, s) 8.8 (1H, s), 8.3 (1H, s), 8.0 (2H, d), 7.5 (2H, appt), 7.3 (1H, appt), 5.6 (2H, s).

SYNTHETIC METHOD B

EXAMPLE 2

N-[5-(2,3-Difluorophenyl)-1H-pyrazolo[3,4-c]pyridin-3-yl]isobutyramide 5-(2,3-Difluorophenyl)-1H-pyrazolo[3,4-c]pyridin-3-ylamine (Description 3; 100 mg, 0.41 mmol) was reacted with isobutyryl chloride (43 uL, 0.41 mmol) in pyridine (0.5 mL) in a manner analogous to that described in Example 1. Chromatography on silica gel using 4% v/v methanol in dichloromethane as eluent afforded the title compound as a solid.

MS (APCI+ve): [M+H]$^+$ at m/z 317 (C16H$_{14}$F$_2$N$_4$O) requires [M+H]$^+$ at m/z 317).

1H NMR δ (DMSO-d$_6$) 13.35 (1H, br s), 10.6 (1H, s), 9.1 (1H, s), 8.3 (1H, s), 7.8 (1H, m), 7.45 (1H, m), 7.3 (1H, m), 2.8 (1H, m) and 1.15 (6H,d).

The starting material for Example 2 may be prepared according to Description 3 below.

Description 3

5-(2,3-Difluorophenyl)-1H-pyrazolo[3,4-c]pyridin-3-ylamine

Hydrazine hydrate (0.52 ml, 10.7 mmol) was added to a stirred solution of 5-chloro-2-(2,3-difluorophenyl)isonicotinonitrile (1.22 g, 4.9 mmol) in pyridine (12.5 mL). The reaction mixture was stirred at reflux for 2 hours, allowed to cool and concentrated. Purification by column chromatography using a gradient of 5–10% methanol in dichloromethane as eluent afforded the title compound as a solid.

MS (APCI+ve): [M+H]$^+$ at m/z 247 (C$_{12}$H$_8$F$_2$N$_4$ requires [M+H]$^+$ at m/z 247).

1H NMR δ (DMSO-d$_6$) 12.1 (1H, s), 8.85 (1H, s), 8.2 (1H, s), 7.8 (1H, t), 7.4 (1H, m), 7.3 (1H, m), 5.7 (2H, s).

SYNTHETIC METHOD C

EXAMPLE 4

1-Methyl4-piperidinecarboxylic acid [5-(2,3-difluorophenyl)-1H-pyrazolo[3,4-c]pyridin-3-yl]amide hydrochloride 1-Methyl-4-piperidinecarbonyl chloride hydrochloride (400 mg, 2.02 mmol) was added to a solution of 5-(2,3-difluorophenyl)-1H-pyrazolo[3,4-c]pyridin-3-ylamine (100 mg, 0.41 mmol) in pyridine (4.5 mL). The reaction mixture was stirred at reflux for 48 hours, allowed to cool and concentrated. Purification by column chromatography using 20% v/v of a 2M methanolic ammonia solution in chloroform as eluent, and subsequent treatment of the product with 1M hydrogen chloride in ether afforded the title compound as a solid.

MS (APCI+ve): [M+H]$^+$ at m/z 372 (C$_{19}$H$_{19}$F$_2$N$_5$O requires [M+H]$^+$ at m/z 372).

1H NMR δ (DMSO-d$_6$) 13.5 (1H, br s), 10.9 (1H, s), 10.25 (1H, br s), 9.1 (1H, s), 8.3 (1H, s), 7.8 (1H, t), 7.45 (1H, q), 7.3 (1H, m), 3.5 (2H, d), 3.0 (2H, q), 2.75 (3H, s), 2.1 (2H, m) and 1.95 (2H, m).

SYNTHETIC METHOD D

EXAMPLE 15

Cyclopropanecarboxylic acid [5-(6-methylpyridin-3-yl)-1H-pyrazolo[3,4-c]pyridin-3-yl]amide Cyclopropanecarboxylic acid [1-(1-cyclopropylmethanoyl)-5-(6-methylpyridin-3-yl)-1H-pyrazolo[3,4-c]pyridin-3-yl]amide (Description 4; 196 mg, 0.542 mmol), was dissolved in piperidine (2 mL) and stirred at room temperature for 16 hours. The piperidine was removed in vacuo, and the resulting oily residue was triturated with water to give the title compound as a solid.

MS (APCI+ve): [M+H]$^+$ at m/z 294 (C$_{16}$H$_{15}$N$_5$O requires [M+H]$^+$ at m/z 294).

$^1$H NMR δ (DMSO-d$_6$): 0.91 (4H, m), 1.91 (1H, br m), 3.30 (3H, singlet obscured by water signal), 7.34 (1H, d), 8.22 (1H, d), 8.32 (1H, s), 9.05 (2H d,). NH protons presumed exchanged with solvent.

The starting material for Example 15 may be prepared according to Description 4 below.

Description 4

Cyclopropanecarboxylic acid [1-(1-cyclopropyl-methanoyl)-5-(6-methylpyridin-3-yl)-1H-pyrazolo[3,4-c]pyridin-3-yl]amide Cyclopropanecarbonyl chloride (186 mg, 1.776 mmol) was added to a stirred solution of 5-(6-methylpyridin-3-yl)-1H-pyrazolo[3,4-c]pyridin-3-ylamine (200 mg, 0.888 mmol) in anhydrous pyridine (5 mL) and the reaction was heated under reflux for 16 hours. The solvent was removed in vacuo, and the residue chromatographed on silica gel using 10% v/v methanol in dichloromethane as eluent to afford the title compound as a solid.

MS (APCI+ve): [M+H]$^+$ at m/z 362 (C$_{20}$H$_{19}$N$_5$O$_2$ requires [+H]$^+$ at m/z 362).

$^1$H NMR δ (DMSO-$_6$): 0.94 (4H, m), 1.21 (4H, m), 2.09 (1H, br m), 2.54 (3H, s) 3.02 (1H, m), 7.40 (1H, d), 8.29 (1H, d), 8.55 (1H, s), 9.11 (1H, s), 9.66 (1H, s) 11.35 (1H, br s).

SYNTHETIC METHOD E

EXAMPLE 20

N-(5-Phenyl-1H-pyrazolo[3,4-c]pyridin-3-yl)4-(piperidin-1-yl)butyramide bitartrate Salt 3-Amino-5-phenyl-1H-pyrazolo[3,4-c]pyridine (0.2 g, 0.951 mmol) was added to the hydrochloride salt of 4-(piperidin-1-yl)butyric acid chloride (0.861 g, 3.81 mmol) in dry pyridine (10 mL) and the mixture heated at reflux under argon for 24 hours. After being allowed to cool, the resulting solid (a bis-amide) was collected and dried. The bis-amide was dissolved in dichloromethane (18 mL) and shaken with polyamine resin (1.107 g, 3.2 mmol/g, 4 equiv.) for 72 hours. After filtration, the resin was washed sequentially with dichloromethane (3×10 mL) followed by 10% v/v methanol in dichloromethane (3×10 mL) and solvents evaporated to afford the crude product, which was purified firstly by preparative HPLC using a gradient elution of 10–90% acetonitrile (containing 0.01% trifluoroacetic acid) in water (containing 0.1% trifluoroacetic acid), followed by passage of the product fractions through an SCX column. Product was retained on the column during washing with methanol (20 mL) and then eluted with 0.5N ammonia in methanol (20 mL) to afford the title compound as the free base.

A solution of this free base in methanol (3 mL) was mixed with an equivalent of tartaric acid in methanol (3 mL) and then evaporated to dryness. The residue was triturated with acetone then dried under high vacuum to afford the title compound as a solid.

MS (AP+ve): [M+H]$^+$ at m/z 364 ($C_{21}H_{25}N_5O$ requires [M+H]$^+$ at m/z 364)

$^1$H NMR δ (DMSO-$d_6$): 1.48 (2H, m), 1.64 (4H, m), 1.94 (2H, m), 2.45–2.60 (2H, m overlapped by DMSO signal), 2.70–3.95 (6H, m, partly overlapped by water signal), 4.02 (2H, s), 7.37 (1H, t), 7.49 (2H, t), 8.02 (2H, d), 8.32 (1H, d), 9.03 (1H, d), 10.74 (1H, br s) and 13.25 (1H, br s). The remaining acidic protons and the hydroxyl protons of the bitartrate were not observed and these are presumed exchanged with the water signal.

SYNTHETIC METHOD F

EXAMPLE 20

Cyclopropanecarboxylic acid N-[5-(quinolin-3-yl)-1H-pyrazolo[3,4]pyridin-3-yl]amide Cyclopropane carbonyl chloride (168 mg, 1.602 mmol) was added to a stirred solution of 5-(quinolin-3-yl)-1H-pyrazolo[3,4-c]pyridin-3-ylamine (200 mg, 0.766 mmol) in anhydrous pyridine (5 mL) and the reaction was heated under reflux for 16 hours. The solvent was then removed in vacuo and the residue re-evaporated from water (10 mL) to yield a solid. This was triturated with saturated aqueous sodium bicarbonate solution and the mixture then left to stand for 0.5 hour until the pH stabilised at pH 9–10. The resulting solid was then collected by filtration, washed with water (3×25 mL) and dried in vacuo. This material was then stirred in piperidine (3 mL) at room temperature for 2 hours. The piperidine was evaporated and the residue triturated with water (5 mL) and with methanol (5 mL) to afford the title compound as a solid.

MS (APCI+ve): [M+H]$^+$ at m/z 330 ($C_{19}H_{15}N_5O$ requires [M+H]$^+$ at m/z 330).

$^1$HNMR δ (DMSO-$d_6$): 0.88 (2H, m), 0.95 (2H, s), 1.99 (1H, br m), 7.65 (1H, t), 7.78 (1H, t), 8.06 (1H, d), 8.13 (1H, d), 8.53 (1H, s), 8.90 (1H, s), 9.12 (1H, s), 9.59 (1H, s), 11.0 (1H, br s) and 13.35 (1H, br s).

Further Examples of the invention are illustrated in Table 1. The further examples described herein were prepared by analogy with Synthetic Methods A–F disclosed above.

TABLE 1

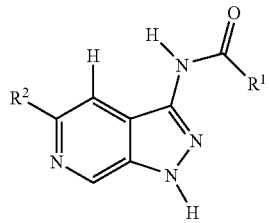

(I)

| Example No | Synthetic Method | R$^1$ | R$^2$ | Calculated Molecular Weight (M) | LC/MS [M + H]$^+$ Observed (Unless [M]- or [M-H]- are indicated) |
|---|---|---|---|---|---|
| 1 | A | n-Pr | Ph | 280.329 | 281 |
| 2 | B | i-Pr | 2,3-di-F-Ph | 316.31 | 317 |
| 3 | B | cyc-Pentyl | 2,3-di-F-Ph | 342.347 | 343 |
| 4 | C | N-Me-Pipieridin-4-yl | 2,3-di-F-Ph | 371.389 | 372 |
| 5 | B | cyc-Pr | Ph | 278.314 | 279 |
| 6 | B | i-Pr | Ph | 280.329 | 281 |
| 7 | B | i-Pr | 2-Cl-Ph | 314.775 | 315/317 |
| 8 | B | cyc-Pentyl | 2-Cl-Ph | 340.812 | 341/343 |
| 9 | C | (CH2)3(Piperidin-1-yl) | 2-Cl-Ph | 397.908 | 398/400 |
| 10 | B | cyc-Pr | Pyridin-3-yl | 279.302 | 280 |
| 11 | B | i-Pr | Pyridin-3-yl | 281.318 | 282 |
| 12 | C | (CH2)3(4-Et-Piperazin-1-yl) | Pyridin-3-yl | 393.492 | 394 |
| 13 | C | (CH2)3(4-Et-Piperazin-1-yl) | 2-Cl-Ph | 426.949 | 427/429 |
| 14 | C | (CH2)3(Pyrrolidin-1-yl) | 2-Cl-Ph | 383.881 | 384/386 |
| 15 | D | cyc-Pr | 6-Me-Pyridin-3-yl | 293.328 | 294 |
| 16 | D | cyc-Pr | 2-Cl-Ph | 312.759 | 313/315 |
| 17 | C | (CH2)3(Pyrrolidin-1-yl) | Pyridin-3-yl | 350.424 | 351 |
| 18 | C | (CH2)3NMe2 | 2-Cl-Ph | 357.843 | 358/360 |
| 19 | C | (CH2)3(Pyrrolidin-1-yl) | Ph | 349.436 | 350 |
| 20 | E | (CH2)3(Piperidin-1-yl) | Ph | 363.462 | 364 |
| 21 | C | (CH2)3(4-Et-Piperazin-1-yl) | Ph | 392.504 | 393 |
| 22 | B | cyc-Pr | 2,3-di-F-Ph | 314.294 | 315 |
| 23 | F | cyc-Pr | Quinolin-3-yl | 329.362 | 330 |
| 24 | B | cyc-Pr | 6-OMe-Pyridin-3-yl | 309.327 | 310 |
| 25 | D | i-Pr | 5-Ph-Pyridin-3-yl | 357.415 | 358 |
| 26 | C | N-Me-Pipieridin-4-yl | 6-Me-Pyridin-3-yl | 350.424 | 351 |
| 27 | C | (CH2)3(4-Et-Piperazin-1-yl) | 6-Me-Pyridin-3-yl | 407.519 | 408 |

TABLE 1-continued

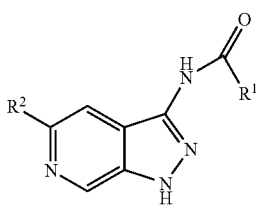

(I)

| Example No | Synthetic Method | R[1] | R[2] | Calculated Molecular Weight (M) | LC/MS [M + H]+ Observed (Unless [M]- or [M-H]- are indicated) |
|---|---|---|---|---|---|
| 28 | C | (CH2)3(4-Et-Piperazin-1-yl) | 2,3-di-F-Ph | 428.484 | 429 |
| 29 | C | (CH2)3(Pyrrolidin-1-yl) | 6-Me-Pyridin-3-yl | 364.451 | 365 |
| 30 | F | 4-NMe2-Ph | 6-Me-Pyridin-3-yl | 372.43 | 373 |
| 31 | C | (CH2)3(4-Et-Piperazin-1-yl) | 4-F-Ph | 410.494 | 411 |
| 32 | C | N-Me-Piperidin-4-yl | 4-F-Ph | 353.399 | 354 |
| 33 | C | N-Me-Piperidin-4-yl | 2,3,4-tri-F-Ph | 389.379 | 390 |
| 34 | C | (CH2)3NMe2 | Ph | 323.398 | 324 |
| 35 | C | (CH2)3NMe2 | 2,3-di-F-Ph | 359.378 | 360 |
| 36 | C | (CH2)3NMe2 | 6-Me-Pyridin-3-yl | 338.413 | 339 |
| 37 | D | [4-[CH2(Pyrrolidin-1-yl)]-Ph] | 4-F-Ph | 415.47 | 416 |
| 38 | C | N-Me-Piperidin-4-yl | 5-Ph-Pyridin-3-yl | 412.495 | 413 |
| 39 | C | (CH2)3(Pyrrolidin-1-yl) | 2,3-di-F-Ph | 385.416 | 386 |
| 40 | C | [4-[CH2(Pyrrolidin-1-yl)]-Ph] | 2,3-di-F-Ph | 433.46 | 434 |
| 41 | C | N-Me-Piperidin-4-yl | Ph | 335.409 | 336 |
| 42 | C | [4-[CH2(Pyrrolidin-1-yl)]-Ph | Ph | 397.48 | 398 |
| 43 | C | (CH2)3NMe2 | 4-F-Ph | 341.388 | 342 |
| 44 | C | (CH2)3NMe2 | 5-Ph-Pyridin-3-yl | 400.84 | 401 |
| 45 | C | (CH2)3(4-Et-Piperazin-1-yl) | 5-Ph-Pyridin-3-yl | 469.59 | 470 |
| 46 | C | (CH2)3NMe2 | Quinolin-3-yl | 374.446 | 375 |
| 47 | C | (CH2)3(4-Et-Piperazin-1-yl) | Quinolin-3-yl | 443.552 | 444 |
| 48 | C | N-Me-Piperidin-4-yl | Quinolin-3-yl | 386.457 | 387 |
| 49 | D | [4-[CH2(Pyrrolidin-1-yl)]-Ph] | 5-Ph-Pyridin-3-yl | 474.565 | 475 |
| 50 | F | cyc-Pentyl | 5-Ph-Pyridin-3-yl | 383.453 | 384 |

What is claimed is:

1. A compound of formula (I):

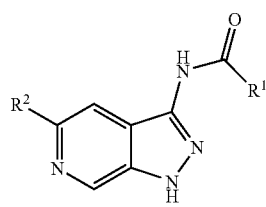

(I)

or a derivative thereof,
wherein;
R[1] is unsubstituted or substituted alkyl, unsubstituted or substituted cycloalkyl, unsubstituted or substituted alkenyl, unsubstituted or substituted cycloalkenyl, unsubstituted or substituted aryl, aralkyl wherein the aryl and the alkyl moieties may each independently be unsubstituted or substituted, aralkenyl wherein the aryl and alkenyl moieties may each independently be unsubstituted or substituted, unsubstituted or substituted heterocyclyl, or heterocyclylalkyl wherein the heterocyclyl and the alkyl moieties may each independently be unsubstituted or substituted; and R[2] is unsubstituted or substituted aryl or unsubstituted or substituted heteroaryl.

2. The compound as claimed in claim 1 wherein R1 is unsubstituted or substituted alkyl, unsubstituted or substituted cycloalkyl, unsubstituted or substituted aryl, unsubstituted or substituted heterocyclyl, or heterocyclylalkyl wherein the heterocyclyl and the alkyl moieties may each independently be unsubstituted or substituted; and
wherein R[2] is unsubstituted or substituted aryl or unsubstituted or substituted heteroaryl.

3. A compound of formula (IA), (IA)

or a derivative thereof,
wherein;
R[1] is $C_{1-6}$ alkyl, cyclo$C_{3-8}$ alkyl, di($C_{1-6}$ alkyl)aminoalkyl, phenyl optionally substituted by di($C_{1-6}$ alkyl)amino, heterocyclyl wherein the heterocyclyl moiety may be optionally substituted by $C_{1-6}$ alkyl and heterocyclyl$C_{1-6}$ alkyl wherein the heterocyclyl moiety may be optionally substituted by $C_{1-6}$ alkyl and phenyl; and $R^2$ is phenyl optionally substituted by one or more halo atoms, quinolinyl and pyridinyl optionally susbtituted by $C_{1-6}$ alkyl, $C_{1-6}$ alkoxy and phenyl.

4. The compound as claimed in claim 1, wherein $R^1$ is n-propyl, iso-propyl, cyclopropyl, cyclopentyl, 3-dimethylaminopropyl, 4-dimethylaminophenyl, 3-(pyrrolidin-1-yl) propyl, 3-(piperidin-1-yl)propyl, 3-(4-ethylpiperazin-1-yl) propyl, 1-methylpiperidin-4-yl and 4-[(pyrrolidin-1-yl) methyl]phenyl and wherein $R^2$ is as defined in claim 1.

5. The compound as claimed in claim 1, wherein $R^1$ is as defined in claim 1 and wherein $R^2$ is phenyl, 2-chlorophenyl, 2,3-difluorophenyl, 4-fluorophenyl, 2,3,4-trifluorophenyl, pyridin-3-yl, 5-phenylpyridin-3-yl, 6-methylpyridin-3-yl, 6-methoxypyridin-3-yl and quinolin-3-yl.

6. The compound as claimed in claim 1, wherein $R^1$ is n-propyl, iso-propyl, cyclopropyl, cyclopentyl, 3-dimethylaminopropyl, 4-dimethylaminophenyl, 3-(pyrrolidin-1-yl) propyl, 3-(piperidin-1-yl)propyl, 3-(4-ethylpiperazin-1-yl) propyl, 1-methylpiperidin-4-yl and 4-[(pyrrolidin-1-yl) methyl]phenyl and wherein $R^2$ is phenyl, 2-chlorophenyl, 2,3-difluorophenyl, 4-fluorophenyl, 2,3,4-trifluorophenyl, pyridin-3-yl, 5-phenylpyridin-3-yl, 6-methylpyridin-3-yl, 6-methoxypyridin-3-yl and quinolin-3-yl.

7. A pharmaceutical composition which comprises a compound as claimed in claim 1 or a pharmaceutically acceptable derivative thereof, and a pharmaceutically acceptable carrier.

8. A process for the preparation of a compound as claimed in claim 1 or a derivative thereof, which process comprises reaction of a compound of formula (II),

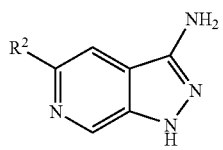

(II)

wherein;

$R^2$ is as defined in formula (I), with a compound of formula (III),

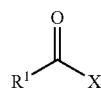

(III)

wherein;

$R^1$ is as defined in formula (I) and X is a leaving group, and thereafter, if required, carrying out one or more of the following optional steps:

(i) converting a compound of formula (I) to a further compound of formula (I);

(ii) removing any necessary protecting group;

(iii) preparing an appropriate derivative of the compound so formed.

9. A process for the preparation of a compound as claimed in claim 1 or a derivative thereof, which process comprises reaction of a compound of formula (V),

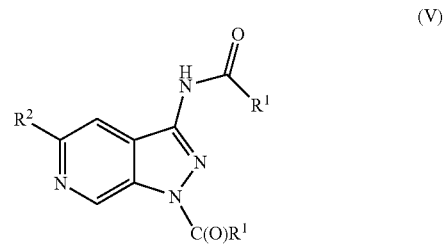

(V)

wherein;

$R^1$ and $R^2$ are as defined in formula (I), with a nucleophile, and thereafter, if required, carrying out one or more of the following optional steps:

(i) converting a compound of formula (I) to a further compound of formula (I);

(ii) removing any necessary protecting group;

(iii) preparing an appropriate derivative of the compound so formed.

10. The compound as claimed in claim 3, wherein $R^1$ is n-propyl, iso-propyl, cyclopropyl, cyclopentyl, 3-dimethylaminopropyl, 4-dimethylaminophenyl, 3-(pyrrolidin-1-yl) propyl, 3-(piperidin-1-yl)propyl, 3-(4-ethylpiperazin-1-yl) propyl, 1-methylpiperidin-4-yl and 4-[(pyrrolidin-1-yl) methyl]phenyl and wherein $R^2$ is as defined in claim 3.

11. The compound as claimed in claim 3, wherein $R^1$ is as defined in claim 3 and wherein $R^2$ is phenyl, 2-chiorophenyl, 2,3-difluorophenyl, 4-fluorophenyl, 2,3,4-trifluorophenyl, pyridin-3-yl, 5-phenylpyridin-3-yl, 6-methylpyridin-3-yl, 6-methoxypyridin-3-yl and quinolin-3-yl.

12. The compound as claimed in claim 3, wherein $R^1$ is n-propyl, iso-propyl, cyclopropyl, cyclopentyl, 3-dimethylaminopropyl, 4-dimethylaminophenyl, 3-(pyrrolidin-1-yl) propyl, 3-(piperidin-1-yl)propyl, 3-(4-ethylpiperazin-1-yl) propyl, 1-methylpiperidin-4-yl and 4-[(pyrrolidin-1-yl) methyl]phenyl and wherein $R^2$ is phenyl, 2-chlorophenyl, 2,3-difluorophenyl, 4-fluorophenyl, 2,3,4-trifluorophenyl, pyridin-3-yl, 5-phenylpyridin-3-yl, 6-methylpyridin-3-yl, 6-methoxypyridin-3-yl and quinolin-3-yl.

* * * * *

UNITED STATES PATENT AND TRADEMARK OFFICE
CERTIFICATE OF CORRECTION

PATENT NO.        : 7,105,532 B2  Page 1 of 1
APPLICATION NO.   : 10/451005
DATED             : September 12, 2006
INVENTOR(S)       : Rawlings et al.

It is certified that error appears in the above-identified patent and that said Letters Patent is hereby corrected as shown below:

On the Title page:

A priority application in Item (30) should be corrected as follows:

(30)   Foreign Application Priority Data
-- Dec. 19, 2000  (GB) .......... 0031070.6 --

Signed and Sealed this

Seventeenth Day of June, 2008

JON W. DUDAS
*Director of the United States Patent and Trademark Office*